(12) United States Patent
Nishimura et al.

(10) Patent No.: US 11,661,474 B2
(45) Date of Patent: May 30, 2023

(54) COMPOSITION, PRODUCTION METHOD FOR COMPOSITION, AND PRODUCTION METHOD FOR UNSATURATED COMPOUND

(71) Applicant: SHOWA DENKO K.K., Tokyo (JP)

(72) Inventors: Norihito Nishimura, Kawasaki (JP); Katsutoshi Ohno, Aizuwakamatsu (JP)

(73) Assignee: SHOWA DENKO K.K., Tokyo (JP)

( * ) Notice: Subject to any disclaimer, the term of this patent is extended or adjusted under 35 U.S.C. 154(b) by 3 days.

(21) Appl. No.: 17/263,596

(22) PCT Filed: Aug. 16, 2019

(86) PCT No.: PCT/JP2019/032117
§ 371 (c)(1),
(2) Date: Jan. 27, 2021

(87) PCT Pub. No.: WO2020/040048
PCT Pub. Date: Feb. 27, 2020

(65) Prior Publication Data
US 2021/0292469 A1    Sep. 23, 2021

(30) Foreign Application Priority Data

Aug. 20, 2018    (JP) .............................. JP2018-154147

(51) Int. Cl.
| | | |
|---|---|---|
| *C08G 18/81* | (2006.01) | |
| *C07C 265/06* | (2006.01) | |
| *C07D 251/34* | (2006.01) | |
| *C08G 18/38* | (2006.01) | |
| *C07C 263/10* | (2006.01) | |
| *C07C 271/60* | (2006.01) | |
| *C09D 175/02* | (2006.01) | |
| *C09J 175/02* | (2006.01) | |
| *C07C 263/20* | (2006.01) | |
| *C07D 251/30* | (2006.01) | |
| *C09D 175/04* | (2006.01) | |
| *C07C 265/04* | (2006.01) | |
| *C07D 231/12* | (2006.01) | |
| *C07C 231/10* | (2006.01) | |

(Continued)

(52) U.S. Cl.
CPC ........ *C08G 18/8116* (2013.01); *C07C 231/10* (2013.01); *C07C 263/10* (2013.01); *C07C 263/20* (2013.01); *C07C 265/04* (2013.01); *C07C 265/06* (2013.01); *C07C 269/02* (2013.01); *C07C 271/60* (2013.01); *C07D 231/12* (2013.01); *C07D 251/30* (2013.01); *C07D 251/34* (2013.01); *C08G 18/3853* (2013.01); *C08G 18/8125* (2013.01); *C09D 175/02* (2013.01); *C09D 175/04* (2013.01); *C09J 175/02* (2013.01); *C09J 175/04* (2013.01)

(58) Field of Classification Search
CPC ............ C08G 18/8116; C08G 18/3853; C08G 18/8125; C07C 265/06; C07C 231/10; C07C 263/20; C07C 269/02; C07C 263/10; C07C 265/04; C07C 271/60; C07D 251/34; C07D 251/30; C07D 231/12; C09D 175/02; C09D 175/04; C09J 175/02; C09J 175/04
See application file for complete search history.

(56) References Cited

U.S. PATENT DOCUMENTS

| | | |
|---|---|---|
| 2,821,544 A | 1/1958 | Holtschmidt |
| 6,245,935 B1 | 6/2001 | Misu et al. |
| 2008/0132597 A1 | 6/2008 | Nozawa et al. |
| 2010/0174109 A1 | 7/2010 | Nozawa et al. |
| 2012/0232183 A1 | 9/2012 | Ooga et al. |
| 2013/0317252 A1* | 11/2013 | Nishimura ............ C07C 263/18 560/331 |

FOREIGN PATENT DOCUMENTS

| | | |
|---|---|---|
| CN | 105884654 A | 8/2016 |
| EP | 3 527 603 A1 | 8/2019 |

(Continued)

OTHER PUBLICATIONS

Yasukazu O, "Degradation Mechanism and Stabilization Technology of Polymer", CMC Technical Library, CMC Publishing Co., Ltd., Apr. 2005, p. 168, Fig. 5.
Taiwanese Office Action for TW108129215 dated Oct. 30, 2020.
International Search Report for PCT/JP2019/032117 dated Nov. 12, 2019 [PCT/ISA/210].

*Primary Examiner* — Rabon A Sergent
(74) *Attorney, Agent, or Firm* — Sughrue Mion, PLLC

(57) ABSTRACT

A composition is provided including a compound (A) represented by Formula (1) and a compound (B) represented by Formula (2), wherein the compound (B) is contained in an amount of 0.00002 to 0.2 parts by mass with respect to 100 parts by mass of the compound (A): $(R_1-COO)_n-R_2-(NCO)_m$ ... (1)
(in Formula (1), $R_1$ is an ethylenically unsaturated group having 2 to 7 carbon atoms; $R_2$ is an (m+n)-valent hydrocarbon group having 1 to 7 carbon atoms; and n and m are each an integer of 1 or 2)

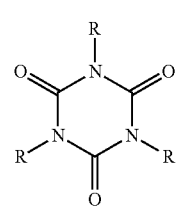

(2)

(in Formula (2), R is $(-R_2-(OCO-R_1)$, and $R_1$ and $R_2$ are the same as those in Formula (1)).

15 Claims, No Drawings

(51) Int. Cl.
*C07C 269/02* (2006.01)
*C09J 175/04* (2006.01)

(56) References Cited

FOREIGN PATENT DOCUMENTS

| | | | |
|---|---|---|---|
| JP | 60-234582 A | 11/1985 |
| JP | 60-234583 A | 11/1985 |
| JP | 06-184256 A | 7/1994 |
| JP | 06-187822 A | 7/1994 |
| JP | 06-322051 A | 11/1994 |
| JP | 11-228523 A | 8/1999 |
| JP | 2007-008828 A | 1/2007 |
| JP | 2007-055993 A | 3/2007 |
| JP | 4273531 B2 | 6/2009 |
| JP | 4823546 B2 | 11/2011 |
| JP | 2016-150922 A | 8/2016 |
| TW | 200837092 A | 9/2008 |
| WO | 2008/143207 A1 | 11/2008 |
| WO | 2011/074503 A1 | 6/2011 |
| WO | 2018/070541 A1 | 4/2018 |

OTHER PUBLICATIONS

* cited by examiner

COMPOSITION, PRODUCTION METHOD FOR COMPOSITION, AND PRODUCTION METHOD FOR UNSATURATED COMPOUND

CROSS REFERENCE TO RELATED APPLICATIONS

This application is a National Stage of International Application No. PCT/JP2019/032117 filed Aug. 16, 2019, claiming priority based on Japanese Patent Application No. 2018-154147 filed Aug. 20, 2018, the content of which is incorporated herein by reference.

TECHNICAL FIELD

The present invention relates to a composition including an unsaturated isocyanate compound, a method for producing the composition, and a method for producing the unsaturated compound.

BACKGROUND ART

Conventionally, unsaturated compounds, such as an unsaturated urethane compound, an unsaturated thiourethane compound, an unsaturated urea compound, and an unsaturated amide compound, have been produced by reacting an unsaturated isocyanate compound with a compound having active hydrogen (a compound having a functional group containing active hydrogen). The unsaturated compounds thus produced have been used for a variety of applications.

For example, the unsaturated compound may be an unsaturated urethane compound produced by reacting 2-methacryloyloxyethyl isocyanate (which hereinafter may be referred to as "MOI", and of which a specific product may be, for example, "Karenz MOI (registered trademark)"), which is an unsaturated isocyanate compound, with polyalkylene glycol, which is a compound having a hydroxyl group. For a method for producing the unsaturated isocyanate compound, several methods are known, such as a method in which phosgene is allowed to react with an amine having an ethylenic double bond and to perform thermal decomposition (see, for example, Patent Document 1). It has been proposed that the above-mentioned unsaturated urethane compound be used as a material for contact lenses (see, for example, Patent Document 2), a material for a solid solvent in a solid polymer electrolyte (for example, see Patent Document 3), and a material for immobilizing a biological material (see, for example, Patent Documents 4 and 5).

In addition, Patent Document 6 describes an unsaturated urea compound obtained by reacting MOI with an organopolysiloxane having amino groups at both ends of the molecular chain. Patent Document 6 describes that this unsaturated urea compound is used as a material for a radiation-curable adhesive organopolysiloxane composition.

Patent Document 7 describes a urethane acrylate synthesized by reacting a product, which has been obtained by reacting a dimerdiol with a polyisocyanate, with an unsaturated isocyanate compound such as MOI. In addition, Patent Document 7 describes a curable composition including this urethane acrylate.

Examples of the unsaturated isocyanate compound used as a material for the unsaturated compounds include, in addition to MOI, 2-acryloyloxyethyl isocyanate (which hereinafter may be referred to as "AOI", and of which a specific product may be, for example, "Karenz AOI (registered trademark)") and methacryloyl isocyanate (which hereinafter may be referred to as "MAI"). MOI, AOI, and MAI are produced industrially, are commercially available, and easily obtainable.

MOI is synthesized by reacting isopropenyl oxazoline or 2-aminoethyl methacrylate hydrochloride with phosgene. AOI is synthesized by reacting 2-vinyloxazoline or 2-aminoethyl acrylate hydrochloride with phosgene. MAI is synthesized by reacting methacrylic acid amide with oxalyl chloride.

The unsaturated isocyanate compound synthesized as described above contains impurities such as by-products and catalyst residues. Therefore, after synthesis of the unsaturated isocyanate compound, an operation of removing the impurities therefrom to increase the purity is generally performed (see, for example, Patent Documents 8 and 9).

In addition, conventionally, the quality of the synthesized unsaturated isocyanate compound is determined using various methods. Specifically, the following methods may be mentioned: a method for checking the appearance of the unsaturated isocyanate compound such as color and the presence or absence of turbidity, a method for checking the purity of the unsaturated isocyanate compound using gas chromatography, a method for checking a hydrolyzable chlorine content in the unsaturated isocyanate compound by potentiometric titration, and a method for checking soluble impurities in the unsaturated isocyanate compound using gel permeation chromatography (GPC) (see, for example, Patent Document 10).

In general, a polymerization inhibitor is added to an unsaturated isocyanate compound so that the unsaturated isocyanate compound can be stably transported and stored. As the polymerization inhibitor, hydroquinone or the like is used and is added at a concentration that is several tens to several hundreds of ppm. For example, Patent Document 7 describes that in a case where an unsaturated urethane compound is synthesized using an unsaturated isocyanate compound, the polymerization inhibitor is added in an amount of 0.01 to 10 parts by mass with respect to 100 parts by mass of a total amount of components.

CITATION LIST

Patent Document

Patent Document 1: U.S. Pat. No. 2,821,544

Patent Document 2: Japanese Unexamined Patent Application, First Publication No. H6-322051

Patent Document 3: Japanese Unexamined Patent Application, First Publication No. H6-187822

Patent Document 4: Japanese Unexamined Patent Application, First Publication No. S60-234582

Patent Document 5: Japanese Unexamined Patent Application, First Publication No. S60-234583

Patent Document 6: Japanese Unexamined Patent Application, First Publication No. H6-184256

Patent Document 7: PCT International Publication No. WO 2011/074503

Patent Document 8: Japanese Patent No. 4273531

Patent Document 9: Japanese Patent No. 4823546

Patent Document 10: Japanese Unexamined Patent Application, First Publication No. 2007-8828

Non Patent Document

Non Patent Document 1: "Degradation Mechanism and Stabilization Technology of Polymer", CMC Technical Library, CMC Publishing Co., Ltd. (published in April, 2005), p. 168, FIG. 5

SUMMARY OF INVENTION

Technical Problem

Conventional unsaturated isocyanate compounds may undergo unexpected viscosity increase or gelling during storage and/or transportation, although no significant difference in their quality is observed by conventional determination methods. Therefore, there has been a need to improve their stability during storage.

In addition, for conventional unsaturated isocyanate compounds, although no significant difference in their quality is observed by conventional determination methods, in a case where the unsaturated isocyanate compounds are used to produce unsaturated compounds, the reaction products may have rapidly increased viscosity or become gelled during production. Therefore, there has been a need to improve their stability during use.

To improve the stability during storage and use of an unsaturated isocyanate compound, a sufficient amount of a polymerization inhibitor may be added to the unsaturated isocyanate compound.

However, in a case where a large amount of a polymerization inhibitor is added to an unsaturated isocyanate compound and this unsaturated isocyanate compound is used as a raw material to produce an unsaturated compound, a coloring component tends to be produced due to the polymerization inhibitor, along with the unsaturated compound (see, for example, Non Patent Document 1). Therefore, there may have been cases where the produced unsaturated compound is colored.

The present invention has been made in view of the above circumstances, and an object of the present invention is to provide a composition having excellent stability during storage and use, and a method for producing the same.

Solution to Problem

The present inventors carried out intensive studies to achieve the above object. As a result, the present inventors found that a compound (which hereinafter may be referred to as "specific compound") having a specific structure, which is contained as an impurity in an unsaturated isocyanate compound that has undergone purification, is one of the factors that deteriorate stability during storage and use of the unsaturated isocyanate compound. Furthermore, the present inventors carried out repeated studies and found that a concentration of the specific compound in the unsaturated isocyanate compound correlates with occurrence of viscosity increase and gelling in the unsaturated isocyanate compound during storage.

However, a purification method for removing the above-mentioned specific compound from an unsaturated isocyanate compound has not been elucidated as yet. Therefore, the present inventors carried out studies on a purification method for removing the above-mentioned specific compound from an unsaturated isocyanate compound. As a result, the present inventors found that in a case where an unsaturated isocyanate compound is subjected to purification by distillation at a reflux ratio of 2.0 to 4.0, a pressure of 1.0 to 10.0 kPa, and a distillation temperature of 90° C. to 140° C., the above-mentioned specific compound can be removed from the unsaturated isocyanate compound.

Furthermore, the present inventors investigated viscosity increase and gelling during storage of the unsaturated isocyanate compound that was subjected to purification by distillation at the above-mentioned reflux ratio, pressure, and distillation temperature. As a result, the present inventors found that the above-mentioned viscosity increase and gelling can be suppressed in a case where a concentration of the above-mentioned specific compound in the unsaturated isocyanate compound is set to 0.2 parts by mass or lower with respect to 100 parts by mass of the unsaturated isocyanate compound, and thus have completed the present invention.

In addition, the present inventors found that even if the above-mentioned specific compound in the unsaturated isocyanate compound is sufficiently removed by distillation, in a case where the purified product obtained by distillation contains an alkaline component such as ethanolamine, aminoethyl methacrylate, aminoethyl acrylate, or triethylamine, an amount of the above-mentioned specific compound increases. In addition, the present inventors found that in a case where a pH adjustment step, in which a pH of the purified product obtained by distillation is adjusted to 1 to 7, is performed, it is possible to effectively suppress an increase in the amount of the above-mentioned specific compound in the produced composition.

That is, the present invention relates to the following.

In a first aspect of the present invention, the composition shown below is provided.

[1] A composition, including: a compound (A) represented by Formula (1); and a compound (B) represented by Formula (2), wherein the compound (B) is contained in an amount of 0.00002 to 0.2 parts by mass with respect to 100 parts by mass of the compound (A), $$(R_1\text{—COO})_n\text{—}R_2\text{—}(NCO)_m \quad (1)$$

(in Formula (1), $R_1$ is an ethylenically unsaturated group having 2 to 7 carbon atoms; $R_2$ is an (m+n)-valent hydrocarbon group having 1 to 7 carbon atoms and may contain an ether group; and n and m are each an integer of 1 or 2)

(2)

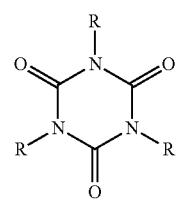

(in Formula (2), R is (—$R_2$—(OCO—$R_1$), and $R_1$ and $R_2$ are the same as those in Formula (1)).

The composition according to the first aspect of the present application also preferably has the following features [2] to [9]. It is also preferable that these features be combined with each other.

[2] The composition according to [1], wherein the compound (A) is at least one compound selected from the group consisting of 2-methacryloyloxyethyl isocyanate, 2-(isocyanatoethyloxy)ethyl methacrylate, 2-acryloyloxyethyl isocyanate, 2-(isocyanatoethyloxy)ethyl acrylate, and 1,1-bis(acryloyloxymethyl)ethyl isocyanate.

[3] The composition according to [1] or [2], wherein a pH of the composition is 1 to 7.

[4] The composition according to any one of [1] to [3], wherein a content of the compound (A) in the composition is 95.0% by mass or higher.

[5] The composition according to any one of [1] to [4], wherein a pH of the composition is 2 to 5.

[6] The composition according to any one of [1] to [5], wherein the content of the compound (A) in the composition is 98.0% to 99.9% by mass.

[7] The composition according to any one of [1] to [6], wherein n and m are each 1.

[8] The composition according to any one of [1] to [7], wherein $R_1$ is $CH_2$=$C(CH_3)$— or a vinyl group; and $R_2$ is an ethylene group, a methylene group, or —$CH_2CH_2OCH_2CH_2$—.

[9] The composition according to any one of [1] to [8], wherein $R_1$ is $CH_2$=$C(CH_3)$— or a vinyl group; $R_2$ is an ethylene group; and n and m are each 1.

In a second aspect of the present invention, the following method for producing a composition is provided.

[10] A method for producing a composition, including: a step of producing a mixture that includes a compound (A) represented by Formula (1) and a compound (B) represented by Formula (2), wherein the compound (B) is contained in an amount of higher than 0.2 parts by mass with respect to 100 parts by mass of the compound (A); and a purification step, wherein the mixture is subjected to purification by distillation at a reflux ratio of 2.0 to 4.0, a pressure of 1.0 to 10.0 kPa, and a distillation temperature of 90° C. to 140° C., to obtain a purified product, and a pH of the purified product is adjusted to 1 to 7, $(R_1$—$COO)_n$—$R_2$—$(NCO)_m$ . . . (1) (in Formula (1), $R_1$ is an ethylenically unsaturated group having 2 to 7 carbon atoms; $R_2$ is an (m+n)-valent hydrocarbon group having 1 to 7 carbon atoms and may contain an ether group; and n and m are each an integer of 1 or 2)

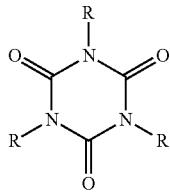

(2)

(in Formula (2), R is (—$R_2$—(OCO—$R_1$), and $R_1$ and $R_2$ are the same as those in Formula (1)).

The method for producing a composition according to the second aspect of the present application also preferably has the following feature [11].

[11] The method according to [4], wherein in the composition obtained by the purification step, the compound (B) is contained in an amount of 0.00002 to 0.2 parts by mass with respect to 100 parts by mass of the compound (A).

In a third aspect of the present application, the following method for producing an unsaturated compound is provided.

[12] A method for producing an unsaturated compound, including: a step of mixing the composition according to any one of [1] to [3] with a compound having active hydrogen to react the compound (A) contained in the composition with the compound having active hydrogen, thereby obtaining a reaction product.

The production method according to the third aspect of the present application also preferably has the following features [13] to [15]. It is also preferable that these features be combined with each other.

[13] The method for producing an unsaturated compound according to [12], wherein the compound having active hydrogen is an alcohol, a thiol, an amine, or a carboxylic acid.

[14] The method for producing an unsaturated compound according to [12] or [13], wherein the reaction product is an unsaturated urethane compound, an unsaturated thiourethane compound, an unsaturated urea compound, or an unsaturated amide compound.

[15] The method for producing an unsaturated compound according to [12] or [13], wherein the reaction product is any one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

Advantageous Effects of Invention

The composition of the present invention is a composition including the compound (A) represented by Formula (1) and the compound (B) represented by Formula (2), in which the compound (B) is contained in an amount of 0.00002 to 0.2 parts by mass with respect to 100 parts by mass of the compound (A). Therefore, the composition hardly undergoes unexpected viscosity increase or gelling during storage and transportation, and thus has excellent stability during storage. In addition, in a case where the composition of the present invention is used to produce an unsaturated compound, the composition causes a reaction product to hardly undergo rapid viscosity increase and/or gelling, which tends to occur during production, and thus has excellent stability during use.

The composition of the present invention has excellent stability during storage and use. Therefore, the composition of the present invention does not need to include a large amount of a polymerization inhibitor that produces a coloring component. Accordingly, the unsaturated compound produced by using the composition of the present invention can be prevented from being colored by the coloring component produced by the polymerization inhibitor.

In the method for producing a composition of the present invention, a mixture including the compound (A) represented by Formula (1) and the compound (B) represented by Formula (2), in which the compound (B) is contained in an amount of higher than 0.2 parts by mass with respect to 100 parts by mass of the compound (A), is subjected to purification by distillation at a reflux ratio of 2.0 to 4.0, a pressure of 1.0 to 10.0 kPa, and a distillation temperature of 90° C. to 140° C., to obtain a purified product, and a pH of the thus obtained purified product is adjusted to 1 to 7. As a result, a composition is obtained, in which the content of the compound (B) is 0.00002 to 0.2 parts by mass with respect to 100 parts by mass of the compound (A). Therefore, according to the method for producing a composition of the present invention, the composition of the present invention, in which the compound (B) that affects the stability during storage and use of the composition has been sufficiently removed from the mixture, can be produced in a high yield. In addition, in the method for producing a composition of the present invention, the pH of the purified product obtained by distillation is adjusted to 1 to 7, in the purification step. Accordingly, the produced composition has a pH of 1 to 7, which makes it difficult to increase the amount of the compound (B).

The method for producing an unsaturated compound of the present invention includes a step of mixing the composition of the present invention with the compound having active hydrogen so that the compound (A) contained in the composition reacts with the compound having active hydrogen, thereby obtaining a reaction product. In the method for producing an unsaturated compound of the present invention, the composition used as a material includes the compound (B) in an amount of 0.00002 to 0.2 parts by mass with respect to 100 parts by mass of the compound (A), which causes the reaction product to hardly undergo a rapid viscosity increase or gelling during the production, and allows excellent productivity to be achieved.

DESCRIPTION OF EMBODIMENTS

Hereinafter, preferred embodiments of the present invention will be described.

The following embodiments will be specifically described to better understand the gist of the invention, although the present invention is not limited to these embodiments unless otherwise specified. Omission, modification, substitution, and/or addition may be made, if necessary, with respect to amount, type, proportion, number, position, or the like, within the scope of the present invention.

In addition, the pressure described in the present specification is an absolute pressure.

"Composition"

The composition of the present embodiment includes an unsaturated isocyanate compound. The composition of the present embodiment includes a compound (A) represented by Formula (1) and a compound (B) represented by Formula (2). In the composition of the present embodiment, the content of the compound (A) is preferably 95.0% by mass or higher; however, the present invention is not limited to this example. In addition, in the composition of the present embodiment, the compound (B) is contained in an amount of 0.00002 to 0.2 parts by mass with respect to 100 parts by mass of the compound (A).

(in Formula (1), $R_1$ is an ethylenically unsaturated group having 2 to 7 carbon atoms; $R_2$ is an (m+n)-valent hydrocarbon group having 1 to 7 carbon atoms and may contain an ether group; and n and m are each an integer of 1 or 2)

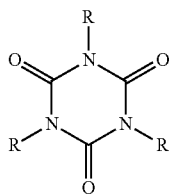

(in Formula (2), R is $(-R_2-(OCO-R_1)$, and $R_1$ and $R_2$ are the same as those in Formula (1)).

In Formulas (1) and (2), $R_1$ is an ethylenically unsaturated group having 2 to 7 carbon atoms. The number of ethylenically unsaturated bonds contained in $R_1$ may be 1 or 2 or more. In a case where $R_1$ has 6 or more carbon atoms, reactivity of the ethylenically unsaturated group decreases. Thus, $R_1$ is preferably an ethylenically unsaturated group having 2 to 5 carbon atoms. The ethylenically unsaturated group preferably has 2 to 3 carbon atoms or 4 to 5 carbon atoms. Among the ethylenically unsaturated groups having 2 to 5 carbon atoms, in particular, $R_1$ is preferably $CH_2=C(CH_3)-$ or a vinyl group from the viewpoint of easy availability of raw material.

In Formulas (1) and (2), $R_2$ is an (m+n)-valent hydrocarbon group having 1 to 7 carbon atoms which may be linear or branched. The (m+n)-valent hydrocarbon group represented by $R_2$ preferably has any of 2 to 4 carbon atoms, and more preferably has 2 carbon atoms. $R_2$ may contain an ether group. $R_2$ is preferably an ethylene group, a methylene group, or $-CH_2CH_2OCH_2CH_2-$, from the viewpoint of easy availability of raw material.

In Formulas (1) and (2), $R_1$ and $R_2$ are the same.

In Formula (1), n and m are each an integer of 1 or 2, and both are preferably 1 from the viewpoint of easy synthesis.

Specific examples of the compound (A) represented by Formula (1) include a compound selected from the group consisting of 2-methacryloyloxyethyl isocyanate, 3-methacryloyloxy-n-propyl isocyanate, 2-methacryloyloxyisopropyl isocyanate, 4-methacryloyloxy-n-butyl isocyanate, 2-methacryloyloxy-tert-butyl isocyanate, 2-methacryloyloxybutyl-4-isocyanate, 2-methacryloyloxybutyl-3-isocyanate, 2-methacryloyloxybutyl-2-isocyanate, 2-methacryloyloxybutyl-1-isocyanate, 5-methacryloyloxy-n-pentyl isocyanate, 6-methacryloyloxy-n-hexyl isocyanate, 7-methacryloyloxy-n-heptyl isocyanate, 2-(isocyanatoethyloxy)ethyl methacrylate, 3-methacryloyloxyphenyl isocyanate, 4-methacryloyloxyphenyl isocyanate, 2-acryloyloxyethyl isocyanate, 3-acryloyloxy-n-propyl isocyanate, 2-acryloyloxyisopropyl isocyanate, 4-acryloyloxy-n-butyl isocyanate, 2-acryloyloxy-tert-butyl isocyanate, 2-acryloyloxybutyl-4-isocyanate, 2-acryloyloxybutyl-3-isocyanate, 2-acryloyloxybutyl-2-isocyanate, 2-acryloyloxybutyl-1-isocyanate, 5-acryloyloxy-n-pentyl isocyanate, 6-acryloyloxy-n-hexyl isocyanate, 7-acryloyloxy-n-heptyl isocyanate, 2-(isocyanatoethyloxy)ethyl acrylate, 3-acryloyloxyphenyl isocyanate, 4-acryloyloxyphenyl isocyanate, 1,1-bis(methacryloyloxymethyl)methyl isocyanate, 1,1-bis(methacryloyloxymethyl)ethyl isocyanate, 1,1-bis(acryloyloxymethyl)methyl isocyanate, 1,1-bis(acryloyloxymethyl)ethyl isocyanate, and 2'-pentenoyl-4-oxyphenyl isocyanate. Among these compounds, in particular, from the viewpoints of easy synthesis and easy availability of raw material, the compound (A) is preferably 2-methacryloyloxyethyl isocyanate (of which a specific product is, for example, Karenz MOI (registered trademark)), 2-acryloyloxyethyl isocyanate (of which a specific product is, for example, Karenz AOI (registered trademark)), 2-(isocyanatoethyloxy)ethyl methacrylate (of which a specific product is, for example, Karenz MOI-EG (registered trademark)), 2-(isocyanatoethyloxy)ethyl acrylate (AOI-EG), or 1,1-bis(acryloyloxymethyl)ethyl isocyanate (of which a specific product is, for example, Karenz BEI (registered trademark)). The products that include Karenz in their registered trademarks, as described in the present specification, are available from Showa Denko K.K.

The content of the compound (A) in the composition of the present embodiment is preferably 95.0% by mass or higher, more preferably 97.0% by mass or higher, and still more preferably 98.0% to 99.9% by mass. The content may be 96.00% to 99.99% by mass or 97.00% to 99.50% by mass, if necessary. In a case where the content of the compound (A) in the composition is 95.0% by mass or higher, the composition can be suitably used as a raw material for producing an unsaturated compound. In addition, it is preferable that the content of the compound (A) be 99.9% by mass or lower, because in such a case, the composition can be efficiently produced using a method of purification by distillation. The content of the compound (A)

in the composition of the present embodiment is not limited to the above-mentioned values, and may be selected in an arbitrary manner, if necessary. For example, a lower limit value of the content of the compound (A) may be 1.0% by mass or higher, 10% by mass or higher, 30% by mass or higher, 50% by mass or higher, 70% by mass or higher, or 80% by mass or higher.

In the compound (B) represented by Formula (2), R is (—$R_2$—OCO—$R_1$), and $R_1$ and $R_2$ are the same as those in Formula (1). The compound (B) has an isocyanurate ring structure. The compound (B) represented by Formula (2) is presumed to be an impurity produced as a by-product in a case where the compound (A) represented by Formula (1) is produced by the production method as described later. The compound (B) deteriorates stability during storage and use of the composition.

In the present embodiment, the content of the compound (B) in the composition is 0.00002 to 0.2 parts by mass with respect to 100 parts by mass of the compound (A). Since the content of the compound (B) in the composition is 0.2 parts by mass or lower with respect to 100 parts by mass of the compound (A), excellent stability during storage and use can be achieved. The content of the compound (B) in the composition is preferably 0.1 part by mass or lower, and more preferably 0.05 parts by mass or lower, with respect to 100 parts by mass of the compound (A), to further improve the stability during storage and use. In addition, since the content of the compound (B) in the composition is 0.00002 parts by mass or higher with respect to 100 parts by mass of the compound (A), the yield at the time of producing the compound (A) can be secured so that the composition can be produced in a high yield. The content of the compound (B) in the composition is preferably 0.0002 parts by mass or higher, and more preferably 0.002 parts by mass or higher with respect to 100 parts by mass of the compound (A), to further improve the yield of the compound (A).

The composition of the present embodiment preferably has a pH in the range of 1 to 7. In a case where the pH of the composition is in the range of 1 to 7, an amount of the compound (B) hardly increases in the composition, and the stability during storage and use is further improved.

In addition to the compound (A) and the compound (B), the composition of the present invention may further include additives as long as an effect of the present invention is not impaired.

Examples of the additive include a polymerization inhibitor such as hydroquinone.

"Method for Producing Composition"

The method for producing a composition of the present embodiment includes a step of producing a mixture that includes the compound (A) represented by Formula (1) and the compound (B) represented by Formula (2), in which the compound (B) is contained in an amount of higher than 0.2 parts by mass with respect to 100 parts by mass of the compound (A); and a purification step, in which the mixture is subjected to purification by distillation at a reflux ratio of 2.0 to 4.0, a pressure of 1.0 to 10.0 kPa, and a distillation temperature of 90° C. to 140° C., to obtain a purified product, and a pH of the purified product is adjusted to 1 to 7. As described above, the content of the compound (A) in the purified product (composition), which is obtained by the purification, is preferably, but not limited to, 95.0% by mass or higher. As described above, the content of the compound (B) in the purified product (composition), which is obtained by the purification, is preferably, but not limited to, 0.00002 to 0.2 parts by mass with respect to 100 parts by mass of the compound (A).

(Step of Producing Mixture)

A method for producing a mixture that includes the compound (A) and the compound (B), in which the compound (B) is contained in an amount of higher than 0.2 parts by mass with respect to 100 parts by mass of the compound (A), may be selected in an arbitrary manner, and examples thereof include a method in which a conventionally known method for producing the compound (A) is used to produce the compound (A) while causing the compound (B) to be simultaneously produced as a by-product.

Specific examples of the method include the following method or the like. First, unsaturated carboxylic acid aminoalkyl ester hydrochloride is synthesized by reacting unsaturated carboxylic acid chloride with aminoalcohol hydrochloride. The unsaturated carboxylic acid aminoalkyl ester hydrochloride is then reacted with carbonyl chloride. As a result, unsaturated carboxylic acid isocyanatoalkyl ester, which is the compound (A), is produced. At the same time, the compound (B) is produced as an impurity, wherein the compound (B) has an isocyanurate ring structure obtained by bonding of three molecules of the compound (A), in which carbon atoms and nitrogen atoms in the isocyanato (—NCO) groups included in the three molecules of the compound (A) are alternately arranged. However, the present invention is not limited to this method.

The thus obtained mixture that includes the compound (A) and the compound (B) generally includes the compound (B) in an amount of higher than 0.2 parts by mass with respect to 100 parts by mass of the compound (A).

An upper limit of the content of the compound (B) in the mixture may be selected in an arbitrary manner. For example, the content of the compound (B) is generally 10.0 parts by mass or lower, preferably 8.0 parts by mass or lower, and more preferably 6 parts by mass or lower, with respect to 100 parts by mass of the compound (A). However, the present invention is not limited to these examples.

In addition, the content of the compound (A) in the mixture may be selected in an arbitrary manner. For example, the content of the compound (A) in the mixture may be, as an example, 55% to 85% by mass, may be 60% to 80% by mass, or may preferably be 65% to 75% by mass. However, the present invention is not limited to these ranges.

(Purification Step)

<Distillation Step>

In the present embodiment, the thus obtained mixture that includes the compound (A) and the compound (B) is subjected to purification by distillation at a reflux ratio (reflux amount/distillation amount) of 2.0 to 4.0, a pressure of 1.0 to 10.0 kPa, and a distillation temperature of 90° C. to 140° C., so that the compound (A) is recovered as a low-boiling component. Since the compound (A) is usually a liquid, no solvent is required.

In the present embodiment, since the purification by distillation is performed at a reflux ratio of 2.0 to 4.0, the compound (B) can be efficiently removed. In a case where the reflux ratio is lower than 2.0, due to the fact that the compound (A) and the compound (B) have similar physical properties, the compound (B) cannot be sufficiently removed, which prevents the content of the compound (B) from being 0.2 parts by mass or lower with respect to 100 parts by mass of the compound (A). The reflux ratio is preferably 2.5 or higher to further decrease the content of the compound (B). In addition, in a case where the reflux ratio is 4.0 or lower, the purification step can be efficiently performed in a short time and the yield of the compound (A) in the composition can be sufficiently secured, which allows the composition to be produced in a high yield. To perform the purification step in a more efficient manner and further improve the yield of compound (A), the reflux ratio is preferably 3.5 or lower.

In the present embodiment, the distillation temperature in the purification step is set to 90° C. to 140° C. In a case where the distillation temperature is lower than 90° C., the compound (A) and the compound (B) cannot be sufficiently separated from each other, which prevents the content of the compound (B) from being 0.2 parts by mass or lower with respect to 100 parts by mass of the compound (A). In addition, in a case where the distillation temperature is 140° C. or lower, the compound (A) is not lost more than necessary and the yield of the compound (A) can be secured, which allows the purification step to be efficiently performed. To sufficiently remove the compound (B) and improve the yield of the compound (A), the distillation temperature is preferably 100° C. to 130° C., and more preferably 110° C. to 120° C.

In the present embodiment, the pressure during distillation in the purification step is 1.0 to 10.0 kPa, and preferably 1.0 to 6.0 kPa. It is preferable that the pressure be 1.0 kPa or higher, because a flooding phenomenon hardly occurs at a distillation temperature of 90° C. to 140° C., and a stable distillation state is easily maintained. It is preferable that the pressure be 10.0 kPa or lower, because the compound (A) and the compound (B) can be easily separated from each other at a distillation temperature of 140° C. or lower, and loss of the compound (A) caused by increased distillation temperature can be suppressed.

In a case where the distillation is performed in the purification step, a polymerization inhibitor may be added to the mixture before starting heating of the mixture. Addition of the polymerization inhibitor to the mixture before starting heating of the mixture makes it possible to prevent the mixture from polymerizing and gelling due to increased temperature caused by the distillation.

The polymerization inhibitor added to the mixture is partially removed by performing the distillation. The polymerization inhibitor remaining in the composition after the distillation prevents the composition from gelling during storage and transportation of the composition, and contributes to improved stability during storage of the composition. The polymerization inhibitor may be added to the composition obtained after the distillation, if necessary.

Specific examples of the polymerization inhibitor include hydroquinone, methoxyhydroquinone, catechol, p-tert-butylcatechol, cresol, 2,6-di-tert-butyl-4-methylphenol (BHT), phenothiazine, and the like.

<pH Adjustment Step>

In the purification step, a pH adjustment step is performed, in which a pH of the purified product obtained by distillation as described above is adjusted to 1 to 7. As a result, a pH of the produced composition becomes 1 to 7, which makes it possible to prevent an amount of the compound (B) from increasing in the composition. Therefore, a composition having better stability during storage and use can be obtained. The pH adjustment step may be a step in which the pH of the purified product obtained by distillation is adjusted to 1 to 6, may preferably be a step in which the pH of such a purified product is adjusted to 2 to 6, and may more preferably be a step in which the pH of such a purified product is adjusted to 2 to 5. The pH of such a purified product may have pH 2 to 4 or pH 2 to 3, if necessary.

In the present embodiment, the pH of the purified product during the pH adjustment step and the pH of the composition obtained by adjusting the pH of the purified product can be measured, for example, by the method shown below. The purified product or composition is placed in a 500 ml beaker and measured using a pH electrode while performing stirring with a stirring bar. As the pH electrode, a non-aqueous solvent-type pH electrode (for example, pH electrode manufactured by HORIBA, Ltd.: 6377-10D), for which a pH calibration has been performed in advance, can be used.

In the present embodiment, the pH value is a pH value measured at a temperature of 20° C. to 25° C.

In the step of adjusting a pH of the purified product obtained by distillation, the time from the end of the purification by distillation (time point when a temperature of the purified product obtained by distillation decreases to 30° C. or lower) to the completion of the pH adjustment (time point when a pH of the purified product obtained by distillation reaches 1 to 7) may be selected in an arbitrary manner, and is preferably 0 to 60 minutes and may be 10 to 45 minutes or the like. To prevent an amount of the compound (B) from increasing in the produced composition, the time is more preferably 10 to 30 minutes. It is most preferable that the purification by distillation and the step of adjusting a pH of the purified product obtained by distillation be continuously performed.

The time from the end of the purification by distillation to the start of the pH adjustment can also be selected in an arbitrary manner. The time until the pH adjustment is started may be 0 to 120 minutes or 0 to 90 minutes. It is preferable to start the pH adjustment as soon as possible. For example, the time may be 0 to 30 minutes and is preferably 0.5 to 20 minutes. Among these, 1 to 10 minutes, 1 to 5 minutes, 1 to 3 minutes, 1 to 2 minutes, or the like may be selected, if necessary.

By performing the above steps, a composition can be obtained, in which the compound (B) is contained in an amount of 0.00002 to 0.2 parts by mass with respect to 100 parts by mass of compound (A). Examples of the content of the compound (A) in the obtained composition include, but are not limited to, 95.0% by mass or higher.

[Method for Producing Unsaturated Compound]

The method for producing an unsaturated compound of the present invention includes a step of mixing the above-described composition with a compound having active hydrogen so that the compound (A) contained in the composition reacts with the compound having active hydrogen, thereby obtaining a reaction product (unsaturated compound).

In the present embodiment, the compound (A) contained in the composition used as a material for the unsaturated compound (reaction product) can be appropriately selected depending on the structure of the unsaturated compound of interest.

In addition, the active hydrogen in the compound having active hydrogen is a hydrogen atom bonded to a nitrogen atom, an oxygen atom, a sulfur atom, or the like, and exhibits high reactivity compared with a hydrogen atom bonded to a carbon atom.

The compound having active hydrogen is not particularly limited, and can be appropriately selected depending on the structure of the unsaturated compound.

For example, in a case where a compound having an active hydrogen-containing group, such as a hydroxyl group, a mercapto group, an amino group (examples thereof including cyclic amine, amide, and imide), and a carboxyl group, is used as the compound having active hydrogen, each reaction as shown below results in the reaction product (unsaturated compound) as shown below.

In a case where the compound (A) contained in the composition is reacted with the compound having a hydroxyl group, the isocyanato group in the compound (A) reacts with the hydroxyl group to produce an unsaturated urethane compound. In the present embodiment, the unsaturated urethane compound means a compound containing an ethylenically unsaturated bond and a urethane bond in the molecule.

In a case where the compound (A) contained in the composition is reacted with the compound having a mercapto group, the isocyanato group in the compound (A) reacts with the mercapto group to produce an unsaturated thiourethane compound. In the present embodiment, the unsaturated thiourethane compound means a compound containing an ethylenically unsaturated bond and a thiourethane bond in the molecule.

In a case where the compound (A) contained in the composition is reacted with the compound having an amino group, the isocyanato group in the compound (A) reacts with the amino group to produce an unsaturated urea compound. In the present embodiment, the unsaturated urea compound means a compound containing an ethylenically unsaturated bond and a urea bond in the molecule.

In a case where the compound (A) contained in the composition is reacted with the compound having a carboxyl group, the isocyanato group in the compound (A) reacts with the carboxyl group to produce an unsaturated amide compound. In the present embodiment, the unsaturated amide compound means a compound containing an ethylenically unsaturated bond and an amide bond in the molecule.

The compound having a hydroxyl group may be selected in an arbitrary manner. Examples thereof include aliphatic alcohol compounds such as ethanol, n- or iso-propanol, butanol or an isomer thereof, pentanol, hexanol, octanol, and decanol; phenol compounds such as phenol, cresol, p-nonylphenol, and methyl salicylate; aliphatic polyols such as ethylene glycol, diethylene glycol, propylene glycol, tetramethylenediol, neopentyl glycol, 1,6-hexanediol, glycerin, trimethylolethane, trimethylolpropane, butanetriol, pentaerythritol, dipentaerythritol, tripentaerythritol, sorbitol, hexanetriol, triglycerol, polyethylene glycol, polypropylene glycol, copolymer of ethylene oxide and propylene oxide, tris(2-hydroxyethyl)isocyanurate, cyclohexanediol, cyclooctanediol, cyclohexanedimethanol, hydroxypropylhexanol, tricyclo[5,2,3,0$^{2,6}$]decanedimethanol, and dicyclohexanediol; aromatic polyols such as dihydroxynaphthalene, dihydroxybenzene, bisphenol-A, bisphenol-F, pyrogallol, xylene glycol, and bisphenol-A (2-hydroxyethyl ether); halogenated polyols such as dibromoneopentyl glycol; hydroxyl group-containing epoxy resins; phenoxy resins; polymeric polyols such as (co)polymers of polyvinyl alcohol and hydroxyethyl (meth)acrylate; terminal hydroxyl group-containing reaction products of organic acids, such as phthalic acid, pyromellitic acid, trimellitic acid, adipic acid, and dimer acid, and the above-mentioned polyols; addition reaction products of the above-mentioned polyols and alkylene oxides (examples thereof including ethylene oxide, propylene oxide, and the like); glucose derivatives such as hydroxyethyl cellulose and nitrocellulose; alcohols containing heterocycles such as orthocarboxylic esters of pentaerythritol (examples of carboxylic acids including formic acid, acetic acid, benzoic acid, and the like); those having a hydrogen group and a mercapto group at the same time, such as 2-mercaptoethanol; oxime-based compounds such as dimethyl ketone oxime, diethyl ketone oxime, and methyl ethyl ketone oxime (MEK oxime); and the like.

Among these, a compound having a hydroxyl group is preferably a polyol, and more preferably an aliphatic polyol.

The compound having a mercapto group may be selected in an arbitrary manner. Examples thereof include monothiols such as 1-butanethiol, 1-pentanethiol, 1-octanethiol, 1-dodecanethiol, n-octadecanthiol, α-toluenethiol, 2-benzimidazolethiol, 2-thiazolin-2-thiol, 2-methyl-2-propanethiol, and o-aminothiophenol; aliphatic polythiols such as hexanedithiol, decandithiol, 1,4-butanediol bisthiopropionate, 1,4-butanediol bisthioglycolate, ethylene glycol bisthioglycolate, ethylene glycol bisthiopropionate, trimethylolpropane tristhioglycolate, trimethylolpropane tristhiopropionate, trimethylolpropane tris(3-mercaptobutyrate), pentaerythritol tetrakisthioglycolate, pentaerythritol tetrakis(2-mercaptopropionate), trimercaptopropionic acid tris(2-hydroxyethyl)isocyanurate, 1,4-dimethylmercaptobenzene, 2,4,6-trimercapto-s-triazine, 2-(N,N-dibutylamino)-4,6-dimercapto-s-triazine, tetraethylene glycol bis(3-mercaptopropionate), trimethylolpropane tris(3-mercaptopropionate), tris(3-mercaptopropionyloxyethyl)isocyanurate, pentaerythritol tetrakis(3-mercaptopropionate), dipentaerythritol hexakis(3-mercaptopropionate), 1,4-bis(3-mercaptobutyryloxy)butane (of which a specific product is, for example, "Karenz MT (registered trademark) BD1"), 1,3,5-tris(3-mercaptobutyloxyethyl)-1,3,5-triazine-2,4,6(1H,3H,5H)-trione (of which a specific product is, for example, "Karenz MT (registered trademark) NR1"), pentaerythritol tetrakis(3-mercaptobutyrate) (of which a specific product is, for example, "Karenz MT (registered trademark) PET"); and the like.

Among these, a compound having a mercapto group is preferably a polythiol, and more preferably an aliphatic polythiol.

The compound having an amino group may be selected in an arbitrary manner. Examples thereof include monoamines such as butylamine, hexylamine and aniline; aliphatic polyamines such as diethylenetriamine, triethylenetetrainine, 1,3- or 1,4-bisaminomethylcyclohexane, isophoronediamine, hexamethylenediamine, and bis(4-aminocyclohexyl)methane; aromatic polyamines such as m- or p-xylylene diamine, bis(4-aminophenyl)methane, and 2,4- or 2,6-tolylene diamine; glucosamines such as chitosan; silicone compounds such as bis(3-aminopropyl)polydimethylsiloxane and bis(3-aminopropyl)polydiphenylsiloxane; heterocyclic compounds such as imidazole, s-caprolactam, and imide phthalate; amides; imides; 2-[(3,5-dimethylpyrazolyl)carbonylainino]ethyl methacrylate (of which a specific product is, for example, "Karenz MOI-BP (registered trademark)"), 2-[(3,5-dimethylpyrazolyl)carbonylamino]ethyl acrylate, and 3,5-dimethylpyrazole; and the like.

Among these, the compound having an amino group is preferably a polyamine, and more preferably an aliphatic polyamine.

The compound having a carboxyl group may be selected in an arbitrary manner. Examples thereof include monocarboxylic acids such as acetic acid, propionic acid, and decanoic acid; aliphatic and/or aromatic polycarboxylic acids such as succinic acid, adipic acid, phthalic acid, isophthalic acid, terephthalic acid, trimellitic acid, and pyromellitic acid; polymeric polycarboxylic acids such as (co)polymer of polyamic acid and acrylic acid; and the like.

Among these, the compound having a carboxyl group is preferably a polycarboxylic acid, and more preferably an aliphatic and/or aromatic polycarboxylic acid.

Furthermore, as the compound having active hydrogen, a halogen-substituted product, such as a fluorine-substituted product or a chlorine-substituted product, of the above-mentioned compound having active hydrogen may be used. Each of these may be used alone, or two or more thereof may be used in admixture.

Among these, from the viewpoint of versatility, the compound having active hydrogen is preferably a polyol, a polythiol, a polyamine, or a polycarboxylic acid, with the polyol being particularly preferred.

The unsaturated compound (reaction product) is preferably at least one selected from an unsaturated urethane compound, an unsaturated thiourethane compound, an unsaturated urea compound, or an unsaturated amide compound, and more preferably at least one selected from 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

In the reaction between the compound (A) contained in the composition of the present invention and the compound having active hydrogen, proportions used of the compound (A) to the compound having active hydrogen are set in consideration of a ratio of isocyanato group to active hydrogen atom.

The ratio of isocyanato group to active hydrogen atom may be the same as the ratio conventionally applied in the reaction of the compound (A) with the compound having active hydrogen. The ratio of isocyanato group to active hydrogen atom varies depending on types of the compound having active hydrogen.

The compound (A) contained in the composition of the present invention may be reacted with the compound having active hydrogen in the presence of a reaction catalyst. The reaction rate can be regulated by an amount added of the reaction catalyst.

As the reaction catalyst, a known reaction catalyst may be used. Specific examples of the reaction catalyst include dibutyltin dilaurate, copper naphthenate, cobalt naphthenate, zinc naphthenate, triethylamine, 1,4-diazabicyclo[2.2.2]octane, zirconium acetylacetonate, titanium diisopropoxybis (ethylacetacetate), a mixture of bismuth tris(2-ethylhexanoate) and 2-ethylhexanoic acid, and the like. These reaction catalysts may be used alone, or two or more thereof may be used in combination.

In a case where the compound (A) contained in the composition of the present invention is reacted with the compound having active hydrogen, the reaction temperature is preferably −10° C. to 100° C., and more preferably 0° C. to 80° C.

In a case where the compound (A) contained in the composition of the present invention is reacted with the compound having active hydrogen, a polymerization inhibitor may be added, if necessary. As the polymerization inhibitor, a commonly used one may be used, and for example, a phenolic compound, a hydroquinone compound, or the like may be used. Specific examples of the polymerization inhibitor include hydroquinone, methoxyhydroquinone, catechol, p-tert-butylcatechol, cresol, 2,6-di-tert-butyl-4-methylphenol (BHT), and the like.

In addition, during the above-mentioned reaction, various substances such as known light stabilizers, ultraviolet absorbers, antioxidants, dye fillers, and reactive diluents may be added depending on the purpose.

The unsaturated compound (reaction product) is preferably at least one selected from an unsaturated urethane compound, an unsaturated thiourethane compound, an unsaturated urea compound, and an unsaturated amide compound, and more preferably at least one selected from 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

The thus obtained unsaturated compound is preferably used as a material in various fields such as paints or coatings, adhesives or tacky adhesives, photoresists, contact lenses, solid electrolytes, and solidification of physiologically active substances.

The composition of the present embodiment is a composition including the compound (A) represented by Formula (1) and the compound (B) represented by Formula (2), in which the compound (B) is contained in an amount of 0.00002 to 0.2 parts by mass with respect to 100 parts by mass of the compound (A). Therefore, the composition has excellent stability during storage and use. In addition, the composition does not need to include a large amount of a polymerization inhibitor that produces a coloring component. Accordingly, the unsaturated compound produced by using the composition of the present embodiment can be prevented from being colored by the coloring component produced by the polymerization inhibitor.

In addition, since the composition of the present embodiment includes the compound (B) in an amount of 0.00002 parts by mass or higher with respect to 100 parts by mass of the compound (A), the composition can be produced in a high yield.

In the method for producing a composition of the present embodiment, a mixture including the compound (A) represented by Formula (1) and the compound (B) represented by Formula (2), in which the compound (B) is contained in an amount of higher than 0.2 parts by mass with respect to 100 parts by mass of the compound (A), is subjected to purification by distillation at a reflux ratio of 2.0 to 4.0, a pressure of 1.0 to 10.0 kPa, and a distillation temperature of 90° C. to 140° C., to obtain a purified product, and a pH of the purified product is adjusted to 1 to 7. As a result, a composition is obtained, in which the content of the compound (B) is 0.00002 to 0.2 parts by mass with respect to 100 parts by mass of the compound (A). Therefore, according to the method for producing a composition of the present embodiment, the composition of the present invention, in which the compound (B) that affects the stability during storage and use of the composition has been sufficiently removed from the mixture, can be produced in a high yield. In addition, in the method for producing a composition of the present embodiment, a pH of the purified product obtained by distillation is adjusted to 1 to 7, in the purification step. Accordingly, the produced composition has a pH of 1 to 7, which makes it difficult for an amount of the compound (B) to increase.

The composition of the present embodiment may include an alkaline component such as ethanolamine, aminoethyl methacrylate, aminoethyl acrylate, and triethylamine. However, an amount of the compound (B) hardly increases even if there is an alkaline component, because the pH has been adjusted. In a case where an alkaline component is contained, an amount of the alkaline component may be selected in an arbitrary manner. For example, the amount of the alkaline component may be, as an example, 0.00001% to 0.5% by mass, is preferably 0.00002% to 0.4% by mass, and is preferably 0.00002 to 0.2% by mass, with respect to 100% by mass of the entire composition.

The method for producing an unsaturated compound of the present embodiment includes a step of mixing the composition of the present invention with the compound having active hydrogen so that the compound (A) contained in the composition reacts with the compound having active hydrogen, thereby obtaining a reaction product. In the method for producing an unsaturated compound of the present embodiment, the composition used as a material includes the compound (B) in an amount of 0.00002 to 0.2 parts by mass with respect to 100 parts by mass of the compound (A). Therefore, the reaction product hardly undergoes rapid viscosity increase or gelling during the production and excellent productivity is achieved.

EXAMPLES

Hereinafter, the present invention will be described in detail by way of examples and comparative examples. The examples as shown below are for facilitating understanding of the details of the present invention, and the present invention is not limited to these examples.

Mixtures 1 and 2 were respectively produced by the methods as shown below.

<Mixture 1> (Synthesis of MOI)

250 mL of toluene and 25 g (0.41 mol) of 2-aminoethanol were placed in a 500 mL four-necked flask equipped with a stirrer, a condenser, a thermometer, and an inner tube, heating was performed to 90° C., and about 20 g of hydrogen chloride gas was supplied thereto. Then, 44 g (0.42 mol) of methacrylic acid chloride was added dropwise thereto, and heating was performed at 90° C. for 1 hour. Subsequently, 80 g (0.81 mol) of phosgene was supplied thereto. Then, 0.4 g of phenothiazine and 0.4 g of 2,6-bis-tert-butylhydroxytoluene were added thereto to remove dissolved phosgene and toluene.

By performing the above steps, a mixture 1 was obtained that includes 45 g (0.29 mol) (yield: 71%) of 2-methacryloyloxyethyl isocyanate (MOI), which is a major product (compound (A)), and tris(2-methacryloyloxyethyl)isocyanurate (43,859 mass ppm), which is a by-product (compound (B)).

<Mixture 2> (Synthesis of AOI)

250 mL of toluene and 25 g (0.41 mol) of 2-aminoethanol were placed in a 500 mL four-necked flask equipped with a stirrer, a condenser, a thermometer, and an inner tube, heating was performed to 90° C., and about 20 g of hydrogen chloride gas was supplied thereto. Then, 56 g (0.44 mol) of 3-chloropropionic acid chloride was added dropwise thereto over 90 minutes, and heating was performed at 90° C. for 1 hour. Subsequently, 80 g (0.81 mol) of phosgene was supplied thereto. Then, dissolved phosgene was removed by nitrogen bubbling. Thereafter, 0.4 g of phenothiazine and 0.4 g of 2,6-bis-tert-butylhydroxytoluene were added thereto, 50 g (0.49 mol) of triethylamine was supplied thereto, and heating was performed with stirring at 50° C. for 6 hours. Subsequently, cooling was performed to room temperature, the produced hydrochloride was filtered, and toluene was distilled off.

By performing the above steps, a mixture 2 was obtained that includes 55 g (0.35 mol) (yield: 87%) of 2-acryloyloxyethyl isocyanate (AOI), which is a major product (compound (A)), and tris(2-acryloyloxyethyl)isocyanurate (68,549 mass ppm), which is a by-product (compound (B)).

<Examples 1 to 6 and Comparative Examples 1 to 8> (MOI)

50 g of the mixture 1 was distilled under the conditions (reflux ratio (reflux amount/distillation amount), distillation temperature, and distillation pressure) as shown in Tables 1 and 2. Subsequently, hydrogen chloride gas was blown into the purified product obtained by distillation, and a pH thereof was adjusted to each pH shown in Tables 1 and 2, to obtain liquid compositions of Examples 1 to 6 and Comparative Examples 1 to 8.

The time taken from the completion of the distillation to the blowing of hydrogen chloride gas into the purified product was set to about 90 minutes. The time taken from the start of the blowing to the completion of the pH adjustment was about 60 minutes.

<Examples 7 to 12 and Comparative Examples 9 to 16> (AOI)

50 g of the mixture 2 was distilled under the conditions (reflux ratio (reflux amount/distillation amount), distillation temperature, and distillation pressure) as shown in Tables 3 and 4. Then, in the same manner as above, hydrogen chloride gas was blown into the purified product obtained by distillation, and a pH thereof was adjusted to each pH shown in Tables 3 and 4, to obtain liquid compositions of Examples 7 to 12 and Comparative Examples 9 to 16.

TABLE 1

| | Example | | | | | |
|---|---|---|---|---|---|---|
| | 1 | 2 | 3 | 4 | 5 | 6 |
| Distillation temperature (° C.) | 110 | 115 | 90 | 100 | 135 | 130 |
| Distillation pressure (kPa) | 2.0 | 2.5 | 1.0 | 1.5 | 6.0 | 6.0 |
| Reflux ratio | 3.5 | 3.0 | 3.5 | 2.5 | 2.0 | 4.0 |
| pH of composition | 2 | 4 | 3 | 4 | 5 | 2 |
| Content of compound A (% by mass) | 98.0 | 98.5 | 98.7 | 98.2 | 99.2 | 99.4 |
| Content of compound B ($\times 10^{-4}$ parts by mass) | 154 | 213 | 759 | 489 | 356 | 623 |
| Yield (%) | 85 | 87 | 90 | 88 | 84 | 78 |
| Viscosity (mPa · sec) | 1.5 | 1.7 | 1.6 | 1.7 | 1.7 | 1.6 |
| Appearance | Not changed | Not changed | Not changed | Not changed | Not changed | Not changed |

TABLE 2

| | Comparative Example | | | | | | | |
|---|---|---|---|---|---|---|---|---|
| | 1 | 2 | 3 | 4 | 5 | 6 | 7 | 8 |
| Distillation temperature (°C.) | 90 | 110 | 135 | 110 | 90 | 100 | 135 | 130 |
| Distillation pressure (kPa) | 1.0 | 2.0 | 6.5 | 2.0 | 1.0 | 1.5 | 6.0 | 6.0 |
| Reflux ratio | 1.0 | 0.2 | 1.5 | 0.5 | 3.5 | 2.5 | 2.0 | 4.5 |
| pH of composition | 3 | 5 | 2 | 1 | 10 | 12 | 9 | 11 |
| Content of compound A (% by mass) | 97.5 | 97.0 | 97.8 | 96.3 | 98.2 | 97.7 | 98.7 | 98.9 |
| Content of compound B (×10$^{-4}$ parts by mass) | 4564 | 2864 | 3365 | 6954 | 8764 | 11123 | 7564 | 8954 |
| Yield (%) | 93 | 90 | 85 | 88 | 90 | 88 | 84 | 78 |
| Viscosity (mPa·sec) | Not measurable | Not measurable | Not measurable | Not measurable | Not measurable | Not measurable | Not measurable | Not measurable |
| Appearance | Syrup-like | Solidified | Syrup-like | Solidified | Syrup-like | Solidified | Syrup-like | Solidified |

TABLE 3

| | Example | | | | | |
|---|---|---|---|---|---|---|
| | 7 | 8 | 9 | 10 | 11 | 12 |
| Distillation temperature (°C.) | 90 | 120 | 130 | 110 | 115 | 125 |
| Distillation pressure (kPa) | 1.5 | 3.5 | 6.5 | 2.5 | 3.0 | 4.5 |
| Reflux ratio | 3.5 | 2.0 | 3.5 | 2.5 | 2.0 | 4.0 |
| pH of composition | 2 | 4 | 3 | 4 | 5 | 2 |
| Content of compound A (% by mass) | 98.6 | 98.5 | 99.4 | 98.2 | 99.2 | 99.6 |
| Content of compound B (×10$^{-4}$ parts by mass) | 165 | 187 | 798 | 503 | 589 | 603 |
| Yield (%) | 88 | 82 | 80 | 86 | 84 | 72 |
| Viscosity (mPa·sec) | 1.6 | 1.8 | 1.6 | 1.7 | 1.7 | 1.6 |
| Appearance | Not changed | Not changed | Not changed | Not changed | Not changed | Not changed |

TABLE 4

| | Comparative Example | | | | | | | |
|---|---|---|---|---|---|---|---|---|
| | 9 | 10 | 11 | 12 | 13 | 14 | 15 | 16 |
| Distillation temperature (°C.) | 90 | 110 | 130 | 110 | 130 | 110 | 115 | 125 |
| Distillation pressure (kPa) | 1.5 | 2.5 | 6.5 | 2.5 | 6.5 | 2.5 | 3.0 | 4.5 |
| Reflux ratio | 1.0 | 0.2 | 1.5 | 0.5 | 3.5 | 2.5 | 2.0 | 4.5 |
| pH of composition | 2 | 4 | 3 | 2 | 11 | 10 | 12 | 10 |
| Content of compound A (% by mass) | 97.5 | 97.0 | 97.8 | 96.3 | 99.4 | 98.2 | 99.2 | 99.6 |
| Content of compound B (×10$^{-4}$ parts by mass) | 2200 | 2654 | 3485 | 7136 | 8897 | 13112 | 8032 | 9065 |
| Yield (%) | 91 | 90 | 81 | 88 | 80 | 86 | 84 | 72 |

TABLE 4-continued

| | Comparative Example | | | | | | | |
|---|---|---|---|---|---|---|---|---|
| | 9 | 10 | 11 | 12 | 13 | 14 | 15 | 16 |
| Viscosity (mPa · sec) | Not measurable | Not measurable | Not measurable | Not measurable | Not measurable | Not measurable | Not measurable | Not measurable |
| Appearance | Syrup-like | Solidified | Syrup-like | Solidified | Syrup-like | Solidified | Syrup-like | Solidified |

Next, the pH of each of the compositions of Examples 1 to 12 and Comparative Examples 1 to 16 was measured by the methods as shown below. Each composition was placed in a 500 ml beaker, and the pH of the composition was measured at a temperature of 20° C. to 25° C. using a pH electrode while stirring the composition with a stirring bar. As the pH electrode, a pH electrode (6377-10D) (manufactured by HORIBA, Ltd.), for which a pH calibration had been performed in advance, was used.

Next, regarding the compositions of Examples 1 to 12 and Comparative Examples 1 to 16, using the methods as shown below, the compound (A) and the compound (B) in each composition were quantified, in which a content (% by mass) of the compound (A) in the composition and a content ($\times 10^{-4}$ parts by mass) of the compound (B) with respect to 100 parts by mass of the compound (A) were determined. The results are shown in Tables 1 to 4.

<Quantification of Compound (A) and Compound (B)>

The quantification was performed by subjecting each composition to gas chromatography (GC) analysis under the following conditions using an internal standard method.

Column: DB-1, inlet temperature of 300° C., detection temperature of 300° C.

Column temperature: 50° C.→(10° C./min)→300° C.

Column flow rate: 1.4 ml/min

Split ratio: 1/50

Detector: FID

In addition, the yield (distillation yield) of each of the compositions of Examples 1 to 12 and Comparative Examples 1 to 16 was determined by the expression as shown below. The results are shown in Tables 1 to 4.

Yield=(mass of composition/theoretical yield)×100 (%)

"Evaluation of Appearance"

100 g of each of the liquid compositions of Examples 1 to 12 and Comparative Examples 1 to 16, which were taken immediately after distillation, was placed in a transparent glass container, and then stored in a sealed state at 25° C. for 30 days under a nitrogen gas atmosphere. The appearance after storage was evaluated by the method shown below.

The transparent glass container, in which the composition was placed, was tilted several times at an angle of about 450 and visually evaluated according to the criteria as shown below. The results are shown in Tables 1 to 4.

"Criteria"

Not changed: The composition flowed down within less than 30 seconds after tilting the glass container.

Syrup-like: The composition flowed down within equal to or longer than 30 seconds and less than 180 seconds after tilting of the glass container.

Solidified: The composition did not flow even after 180 seconds or longer had passed after tilting of the glass container.

"Method for Measuring Viscosity"

The viscosity of each of the compositions of Examples 1 to 12 and Comparative Examples 1 to 16, which had been stored in a sealed state at 25° C. for 30 days, was determined by the method shown below according to JIS-Z 8803:2011. The results are shown in Tables 1 to 4.

For each composition, the kinematic viscosity (cm$^3$/sec) at 25° C. was measured using an Ubbelohde viscometer. For Examples 1 to 6 and Comparative Examples 1 to 8, their viscosity (mPa·sec) was calculated by multiplying the measured value of kinematic viscosity by the density of Karenz MOI (registered trademark) (manufactured by Showa Denko K.K.) as shown below. In addition, for Examples 7 to 12 and Comparative Examples 9 to 16, their viscosity (mPa·sec) was calculated by multiplying the measured value of kinematic viscosity by the density of Karenz AOI (registered trademark) (manufactured by Showa Denko K.K.) as shown below.

(Density of Karenz MOI (registered trademark)) 1.096 g/cm$^3$ (25° C.)

(Density of Karenz AOI (registered trademark)) 1.133 g/cm$^3$ (25° C.)

As shown in Tables 1 to 4, for the compositions of Examples 1 to 12, in each of which compound (B) is contained in an amount of 0.00002 to 0.2 parts by mass with respect to 100 parts by mass of compound (A), their viscosity was sufficiently low after storage at 25° C. for 30 days, and their appearance was evaluated as "not changed".

On the other hand, for the compositions of Comparative Examples 1 to 16, in each of which a content of the compound (B) is higher than 0.2 parts by mass with respect to 100 parts by mass of the compound (A), in a case of being stored at 25° C. for 30 days, their viscosity became too high to measure the viscosity. In addition, for the compositions of Comparative Examples 1 to 16, their appearance was evaluated as "syrup-like" or "solidified".

(Unsaturated Compounds)

<Example 21> (Reaction Product of (Poly)Ol and MOI)

Into a four-necked flask with a capacity of 500 ml, which was equipped with a stirrer, a reflux condenser, and a thermometer, were charged 165 g of polyethylene glycol (number average molecular weight of 660) and 77.5 g of the composition of Example 1 (in which the compound (A) was MOI). Then reaction was allowed to occur for 5 hours while keeping the temperature at 80° C., so that an unsaturated urethane compound 1 was synthesized.

<Example 22> (Reaction Product of (Poly)Ol and MOI)

An unsaturated urethane compound 2 was synthesized in the same manner as in Example 21, except that the composition of Example 6 (in which the compound (A) was MOI) was used in place of the composition of Example 1.

<Comparative Example 21> (Reaction Product of (Poly)Ol and MOI)

An unsaturated urethane compound 3 was synthesized in the same manner as in Example 21, except that the composition of Comparative Example 1 (in which the compound (A) was MOT) was used in place of the composition of Example 1.

<Comparative Example 22> (Reaction Product of (Poly)Ol and MOI)

An unsaturated urethane compound 4 was synthesized in the same manner as in Example 21, except that the composition of Comparative Example 8 (in which the compound (A) was MOT) was used in place of the composition of Example 1.

<Example 23> (Reaction Product of (Poly)Ol and AOI)

Into a four-necked flask with a capacity of 500 ml, which was equipped with a stirrer, a reflux condenser, and a thermometer, were charged 165 g of polyethylene glycol (number average molecular weight of 660) and 70.5 g of the composition of Example 7 (in which the compound (A) was AOI). Reaction was allowed to occur for 5 hours while keeping the temperature at 80° C., so that an unsaturated urethane compound 5 was synthesized.

<Example 24> (Reaction Product of (Poly)Ol and AOI)

An unsaturated urethane compound 6 was synthesized in the same manner as in Example 23, except that the composition of Example 11 (in which the compound (A) was AOI) was used in place of the composition of Example 7.

<Comparative Example 23> (Reaction Product of (Poly)Ol and AOI)

An unsaturated urethane compound 7 was synthesized in the same manner as in Example 23, except that the composition of Comparative Example 9 (in which the compound (A) was AOI) was used in place of the composition of Example 7.

<Comparative Example 24> (Reaction Product of (Poly)Ol and AOI)

An unsaturated urethane compound 8 was synthesized in the same manner as in Example 23, except that the composition of Comparative Example 15 (in which the compound (A) was AOI) was used in place of the composition of Example 7.

The viscosity of a reaction solution, which includes each of the unsaturated urethane compounds 1 to 8 obtained in Examples 21 to 24 and Comparative Examples 21 to 24, was measured at 25° C. according to JIS-Z 8803:2011 using a tuning-fork vibration viscometer (SV-type viscometer (SV-10 type), manufactured by A & D Company, Limited). The results are shown in Tables 5 and 6.

TABLE 5

| | Unsaturated urethane compound | Composition | Content of compound B in composition ($\times 10^{-4}$ parts by mass) | Viscosity (mPa · sec) |
|---|---|---|---|---|
| Example 21 | 1 | Example 1 | 154 | 0.14 |
| Example 22 | 2 | Example 6 | 623 | 0.20 |
| Comparative Example 21 | 3 | Comparative Example 1 | 4564 | Gelled |
| Comparative Example 22 | 4 | Comparative Example 8 | 8954 | Gelled |

TABLE 6

| | Unsaturated urethane compound | Composition | Content of compound B in composition ($\times 10^{-4}$ parts by mass) | Viscosity (mPa · sec) |
|---|---|---|---|---|
| Example 23 | 5 | Example 7 | 165 | 0.17 |
| Example 24 | 6 | Example 11 | 589 | 0.21 |
| Comparative Example 23 | 7 | Comparative Example 9 | 2200 | Gelled |
| Comparative Example 24 | 8 | Comparative Example 15 | 8032 | Gelled |

As shown in Table 5, in Examples 21 and 22 produced using the composition, in which the compound (B) is contained in an amount of 0.00002 to 0.2 parts by mass with respect to 100 parts by mass of the compound (A), the unsaturated urethane compounds 1 and 2 having appropriate viscosity could be obtained, and the unsaturated urethane compounds could be produced without any problem.

On the other hand, in Comparative Examples 21 and 22 produced by using the composition, in which a content of the compound (B) was higher than 0.2 parts by mass with respect to 100 parts by mass of the compound (A), there was no problem in handling at the raw material stage; however, gelling occurred during the production of the unsaturated urethane compounds 3 and 4.

As shown in Table 6, in Examples 23 and 24 produced using the composition, in which the compound (B) is contained in an amount of 0.00002 to 0.2 parts by mass with respect to 100 parts by mass of the compound (A), the unsaturated urethane compounds 5 and 6 having appropriate viscosity could be obtained, and the unsaturated urethane compounds could be produced without any problem.

On the other hand, in Comparative Examples 23 and 24 produced by using the composition, in which the content of the compound (B) was higher than 0.2 parts by mass with respect to 100 parts by mass of the compound (A), the unsaturated urethane compounds 7 and 8 had high viscosity, and part thereof gelled during the production.

<Example 25> (Reaction Product of (Poly)amine and MOI)

Into a four-necked flask with a capacity of 500 ml, which was equipped with a stirrer, a reflux condenser, and a thermometer, were charged 66.4 g of (2-[(3,5-dimethylpyrazolyl)carbonylamino]ethyl methacrylate) (Karenz MOI-BP (registered trademark), manufactured by Showa Denko K.K.) and 77.4 g of 3,5-dimethylpyrazole. 122.6 g of the composition of Example 2 (in which the compound (A) was MOI) was supplied thereto while keeping the temperature at 35° C., and reaction was allowed to occur for 2 hours, so that an unsaturated urea compound 1 was synthesized.

<Example 26> (Reaction Product of (Poly)amine and MOI)

An unsaturated urea compound 2 was synthesized in the same manner as in Example 25, except that the composition of Example 4 (in which the compound (A) was MOI) was used in place of the composition of Example 2.

<Comparative Example 25> (Reaction Product of (Poly)amine and MOI)

An unsaturated urea compound 3 was synthesized in the same manner as in Example 25, except that the composition of Comparative Example 3 (in which the compound (A) was MOI) was used in place of the composition of Example 2.

<Comparative Example 26> (Reaction Product of (Poly)amine and MOI)

An unsaturated urea compound 4 was synthesized in the same manner as in Example 25, except that the composition of Comparative Example 6 (in which the compound (A) was MOI) was used in place of the composition of Example 2.

<Example 27> (Reaction Product of (Poly)amine and AOI)

Into a four-necked flask with a capacity of 1,000 ml, which was equipped with a stirrer, a reflux condenser, and a thermometer, were charged 115.9 g of 3,5-dimethylpyrazole and 155.0 g of 2-acetoxy-1-methoxypropane. 174.0 g of the composition of Example 9 (in which compound (A) was AOI) was supplied thereto while keeping the temperature at 15° C., and reaction was allowed to occur for 30 minutes. Thereafter, 320.0 g of n-hexane was added thereto and cooling was performed to 0° C., to crystallize an unsaturated urea compound 5. The obtained crystal was collected by filtration, and washing was performed with n-hexane. Then, drying under reduced pressure was performed to isolate an unsaturated urea compound 5.

<Example 28> (Reaction Product of (Poly)amine and AOI)

An unsaturated urea compound 6 was synthesized in the same manner as in Example 27, except that the composition of Example 12 (in which the compound (A) was AOI) was used in place of the composition of Example 9.

<Comparative Example 27> (Reaction Product of (Poly)amine and AOI)

An unsaturated urea compound 7 was synthesized in the same manner as in Example 27, except that the composition of Comparative Example 11 (in which the compound (A) was AOI) was used in place of the composition of Example 9.

<Comparative Example 28> (Reaction Product of (Poly)amine and AOI)

An unsaturated urea compound 8 was synthesized in the same manner as in Example 27, except that the composition of Comparative Example 13 (in which the compound (A) was AOI) was used in place of the composition of Example 9.

The viscosity of a reaction solution, which includes each of the unsaturated urethane compounds 1 to 8 obtained in Examples 25 to 28 and Comparative Examples 25 to 28, was measured at 25° C. according to JIS-Z 8803:2011 using a tuning-fork vibration viscometer (SV-type viscometer (SV-10 type), manufactured by A & D Company, Limited). The results are shown in Tables 7 and 8.

TABLE 7

| | Unsaturated urea compound | Composition | Content of compound B in composition ($\times 10^{-4}$ parts by mass) | Viscosity (mPa · sec) |
|---|---|---|---|---|
| Example 25 | 1 | Example 2 | 213 | 0.19 |
| Example 26 | 2 | Example 4 | 489 | 0.24 |
| Comparative Example 25 | 3 | Comparative Example 3 | 3365 | Gelled |
| Comparative Example 26 | 4 | Comparative Example 6 | 11123 | Gelled |

TABLE 8

| | Unsaturated urea compound | Composition | Content of compound B in composition ($\times 10^{-4}$ parts by mass) | Viscosity (mPa · sec) |
|---|---|---|---|---|
| Example 27 | 5 | Example 9 | 798 | 0.26 |
| Example 28 | 6 | Example 12 | 603 | 0.21 |
| Comparative Example 27 | 7 | Comparative Example 11 | 3485 | Gelled |
| Comparative Example 28 | 8 | Comparative Example 13 | 8897 | Gelled |

As shown in Table 7, in Examples 25 and 26 produced using the composition, in which the compound (B) is contained in an amount of 0.00002 to 0.2 parts by mass with respect to 100 parts by mass of the compound (A), the unsaturated urea compounds 1 and 2 having appropriate viscosity could be obtained, and the unsaturated urea compounds could be produced without any problem.

On the other hand, in Comparative Examples 25 and 26 produced by using the composition, in which the content of the compound (B) was higher than 0.2 parts by mass with respect to 100 parts by mass of the compound (A), there was no problem in handling at the raw material stage; however, gelling occurred during the production of the unsaturated urea compounds 3 and 4.

As shown in Table 8, in Examples 27 and 28 produced using the composition, in which the compound (B) is contained in an amount of 0.00002 to 0.2 parts by mass with respect to 100 parts by mass of the compound (A), the unsaturated urea compounds 5 and 6 having appropriate viscosity could be obtained, and the unsaturated urea compounds could be produced without any problem.

On the other hand, in Comparative Examples 25 and 26 produced by using the composition, in which the content of the compound (B) was higher than 0.2 parts by mass with respect to 100 parts by mass of the compound (A), there was no problem in handling at the raw material stage; however, gelling occurred during the production of the unsaturated urea compounds 7 and 8.

<Example 29> (Reaction Product of (Poly)carboxylic Acid and MOI)

Into a four-necked flask with a capacity of 500 ml, which was equipped with a stirrer, a reflux condenser, and a thermometer, were charged 177.3 g of decanoic acid, 156.5 g of the composition of Example 3 (in which the compound (A) was MOI), and 0.8 g of dibutyltin dilaurate. Reaction was allowed to occur for 12 hours while keeping the temperature at 80° C., so that an unsaturated amide compound 1 was synthesized.

<Example 30> (Reaction Product of (Poly)carboxylic Acid and MOI)

An unsaturated amide compound 2 was synthesized in the same manner as in Example 29, except that the composition of Example 4 (in which the compound (A) was MOI) was used in place of the composition of Example 3.

<Comparative Example 29> (Reaction Product of (Poly)carboxylic Acid and MOI)

An unsaturated amide compound 3 was synthesized in the same manner as in Example 29, except that the composition of Comparative Example 2 (in which the compound (A) was MOI) was used in place of the composition of Example 3.

<Comparative Example 30> (Reaction Product of (Poly)carboxylic Acid and MOI)

An unsaturated amide compound 4 was synthesized in the same manner as in Example 29, except that the composition of Comparative Example 7 (in which the compound (A) was MOT) was used in place of the composition of Example 3.

<Example 31> (Reaction Product of (Poly)carboxylic Acid and AOI)

Into a four-necked flask with a capacity of 500 ml, which was equipped with a stirrer, a reflux condenser, and a thermometer, were charged 177.3 g of decanoic acid, 142.4 g of the composition of Example 8 (in which the compound (A) was AOI), and 0.8 g of dibutyltin dilaurate. Reaction was allowed to occur for 12 hours while keeping the temperature at 80° C., so that an unsaturated amide compound 5 was synthesized.

<Example 32> (Reaction Product of (Poly)carboxylic Acid and AOI)

An unsaturated amide compound 6 was synthesized in the same manner as in Example 31, except that the composition of Example 11 (in which the compound (A) was AOI) was used in place of the composition of Example 8.

<Comparative Example 31> (Reaction Product of (Poly)carboxylic Acid and AOI)

An unsaturated amide compound 7 was synthesized in the same manner as in Example 31, except that the composition of Comparative Example 10 (in which the compound (A) was AOI) was used in place of the composition of Example 8.

<Comparative Example 32> (Reaction Product of (Poly)carboxylic Acid and AOI)

An unsaturated amide compound 8 was synthesized in the same manner as in Example 31, except that the composition of Comparative Example 14 (in which the compound (A) was AOI) was used in place of the composition of Example 8.

The viscosity of a reaction solution, which includes each of the unsaturated amide compounds 1 to 8 obtained in Examples 29 to 32 and Comparative Examples 29 to 32, was measured at 25° C. according to JIS-Z 8803:2011 using a tuning-fork vibration viscometer (SV-type viscometer (SV-10 type), manufactured by A & D Company, Limited). The results are shown in Tables 9 and 10.

TABLE 9

| | Unsaturated amide compound | Composition | Content of compound B in composition ($\times 10^{-4}$ parts by mass) | Viscosity (mPa · sec) |
|---|---|---|---|---|
| Example 29 | 1 | Example 3 | 759 | 0.77 |
| Example 30 | 2 | Example 4 | 489 | 0.69 |
| Comparative Example 29 | 3 | Comparative Example 2 | 2864 | Gelled |
| Comparative Example 30 | 4 | Comparative Example 7 | 7564 | Gelled |

TABLE 10

| | Unsaturated amide compound | Composition | Content of compound B in composition ($\times 10^{-4}$ parts by mass) | Viscosity (mPa · sec) |
|---|---|---|---|---|
| Example 31 | 5 | Example 8 | 187 | 0.22 |
| Example 32 | 6 | Example 11 | 589 | 0.28 |
| Comparative Example 31 | 7 | Comparative Example 10 | 2654 | Gelled |
| Comparative Example 32 | 8 | Comparative Example 14 | 13112 | Gelled |

As shown in Table 9, in Examples 29 and 30 produced using the composition, in which the compound (B) is contained in an amount of 0.00002 to 0.2 parts by mass with respect to 100 parts by mass of the compound (A), the unsaturated amide compounds 1 and 2 having appropriate viscosity could be obtained, and the unsaturated amide compounds could be produced without any problem.

On the other hand, in Comparative Examples 29 and 30 produced by using the composition, in which the content of the compound (B) was higher than 0.2 parts by mass with respect to 100 parts by mass of the compound (A), there was no problem in handling at the raw material stage; however, gelling occurred during the production of the unsaturated amide compounds 3 and 4.

As shown in Table 10, in Examples 31 and 32 produced using the composition, in which the compound (B) is contained in an amount of 0.00002 to 0.2 parts by mass with respect to 100 parts by mass of the compound (A), the unsaturated amide compounds 5 and 6 having appropriate viscosity could be obtained, and the unsaturated amide compounds could be produced without any problem.

On the other hand, in Comparative Examples 31 and 32 produced by using the composition, in which the content of the compound (B) was higher than 0.2 parts by mass with respect to 100 parts by mass of the compound (A), there was no problem in handling at the raw material stage; however, gelling occurred during the production of the unsaturated amide compounds 7 and 8.

<Example 33> (Reaction Product of (Poly)thiol and MOI)

Into a four-necked flask with a capacity of 500 ml, which was equipped with a stirrer, a reflux condenser, and a thermometer, were charged 177.3 g of 1-octanethiol and 184.3 g of the composition of Example 3 (in which the compound (A) was MOT). Reaction was allowed to occur for 24 hours while keeping the temperature at 80° C., so that an unsaturated thiourethane compound 1 was synthesized.

<Example 34> (Reaction Product of (Poly)thiol and MOI)

An unsaturated thiourethane compound 2 was synthesized in the same manner as in Example 33, except that the composition of Example 5 (in which the compound (A) was MOI) was used in place of the composition of Example 3.

<Comparative Example 33> (Reaction Product of (Poly)thiol and MOT)

An unsaturated thiourethane compound 3 was synthesized in the same manner as in Example 33, except that the composition of Comparative Example 4 (in which the compound (A) was MOI) was used in place of the composition of Example 3.

<Comparative Example 34> (Reaction Between (Poly)thiol and MOT)

An unsaturated thiourethane compound 4 was synthesized in the same manner as in Example 33, except that the composition of Comparative Example 5 (in which the compound (A) was MOT) was used in place of the composition of Example 3.

<Example 35> (Reaction Product of (Poly)thiol and AOI)

Into a four-necked flask with a capacity of 500 ml, which was equipped with a stirrer, a reflux condenser, and a thermometer, were charged 177.3 g of 1-octanethiol and 167.7 g of the composition of Example 8 (in which the compound (A) was AOI). Reaction was allowed to occur for 24 hours while keeping the temperature at 80° C., so that an unsaturated thiourethane compound 5 was synthesized.

<Example 36> (Reaction Product of (Poly)thiol and AOI)

An unsaturated thiourethane compound 6 was synthesized in the same manner as in Example 35, except that the composition of Example 10 (in which the compound (A) was AOI) was used in place of the composition of Example 8.

<Comparative Example 35> (Reaction Product of (Poly)thiol and AOI)

An unsaturated thiourethane compound 7 was synthesized in the same manner as in Example 35, except that the composition of Comparative Example 12 (in which the compound (A) was AOI) was used in place of the composition of Example 8.

<Comparative Example 36> (Reaction Product of (Poly)thiol and AOI)

An unsaturated thiourethane compound 8 was synthesized in the same manner as in Example 35, except that the composition of Comparative Example 16 (in which the compound (A) was AOI) was used in place of the composition of Example 8.

The viscosity of a reaction solution, which includes each of the unsaturated thiourethane compounds 1 to 8 obtained in Examples 33 to 36 and Comparative Examples 33 to 36, was measured at 25° C. according to JIS-Z 8803:2011 using a tuning-fork vibration viscometer (SV-10 type, manufactured by A & D Company, Limited). The results are shown in Tables 11 and 12.

TABLE 11

| | Unsaturated thiourethane compound | Composition | Content of compound B in composition ($\times 10^{-4}$ parts by mass) | Viscosity (mPa · sec) |
|---|---|---|---|---|
| Example 33 | 1 | Example 3 | 759 | 0.87 |
| Example 34 | 2 | Example 5 | 356 | 0.76 |
| Comparative Example 33 | 3 | Comparative Example 4 | 6954 | Gelled |
| Comparative Example 34 | 4 | Comparative Example 5 | 8764 | Gelled |

TABLE 12

| | Unsaturated thiourethane compound | Composition | Content of compound B in composition ($\times 10^{-4}$ parts by mass) | Viscosity (mPa · sec) |
|---|---|---|---|---|
| Example 35 | 5 | Example 8 | 187 | 0.54 |
| Example 36 | 6 | Example 10 | 503 | 0.68 |
| Comparative Example 35 | 7 | Comparative Example 12 | 7136 | Gelled |
| Comparative Example 36 | 8 | Comparative Example 16 | 9065 | Gelled |

As shown in Table 11, in Examples 33 and 34 produced using the composition, in which the compound (B) is contained in an amount of 0.00002 to 0.2 parts by mass with respect to 100 parts by mass of the compound (A), the unsaturated thiourethane compounds 1 and 2 having appropriate viscosity could be obtained, and the unsaturated thiourethane compounds could be produced without any problem.

On the other hand, in Comparative Examples 33 and 34 produced by using the composition, in which the content of the compound (B) was higher than 0.2 parts by mass with respect to 100 parts by mass of the compound (A), there was no problem in handling at the raw material stage; however, gelling occurred during the production of the unsaturated thiourethane compounds 3 and 4.

As shown in Table 12, in Examples 35 and 36 produced using the composition, in which the compound (B) is contained in an amount of 0.00002 to 0.2 parts by mass with respect to 100 parts by mass of the compound (A), the unsaturated thiourethane compounds 5 and 6 having appropriate viscosity could be obtained, and the unsaturated thiourethane compounds could be produced without any problem.

On the other hand, in Comparative Examples 35 and 36 produced by using the composition, in which a content of the compound (B) was higher than 0.2 parts by mass with respect to 100 parts by mass of the compound (A), there was no problem in handling at the raw material stage; however, gelling occurred during the production of the unsaturated thiourethane compounds 7 and 8.

<Example 37> (Reaction Product of Oxime Compound and MOI)

Into a four-necked flask with a capacity of 500 ml, which was equipped with a stirrer, a reflux condenser, and a thermometer, was charged 167.0 g of 2-butanone oxime (hereinafter also referred to as "MEK oxime"). 293.1 g of the composition of Example 2 (in which the compound (A) was MOT) was supplied thereto while keeping the temperature at 35° C., and reaction was allowed to occur for 2 hours, so that MOI-BM (2-butanone oxime-O-(carbamoylethyl-2-methacrylate)) was synthesized as an unsaturated butanone oxime compound 1. MOI-BM is a mixture of (2-butanone oxime-O-(E)-(carbamoylethyl-2-methacrylate) and 2-butanone oxime-O-(Z)-(carbamoylethyl-2-methacrylate).

A specific product of such MOI-BM may be, for example, Karenz MOI-BM (registered trademark).

<Example 38> (Reaction Product of Oxime Compound and MOT)

An unsaturated butanone oxime compound 2 was synthesized in the same manner as in Example 37, except that the composition of Example 4 (in which the compound (A) was MOT) was used in place of the composition of Example 2.

<Comparative Example 37> (Reaction Product of Oxime Compound and MOT)

An unsaturated butanone oxime compound 3 was synthesized in the same manner as in Example 37, except that the composition of Comparative Example 2 (in which the compound (A) was MOT) was used in place of the composition of Example 2.

<Comparative Example 38> (Reaction Product of Oxime Compound and MOT)

An unsaturated butanone oxime compound 4 was synthesized in the same manner as in Example 37, except that the composition of Comparative Example 6 (in which the compound (A) was MOI) was used in place of the composition of Example 2.

<Example 39> (Reaction Product of Oxime Compound and AOI)

Into a four-necked flask with a capacity of 500 ml, which was equipped with a stirrer, a reflux condenser, and a thermometer, were simultaneously supplied 167.0 g of MEK oxime and 266.7 g of the composition of Example 8 (in which the compound (A) was AOI) while keeping the temperature at 15° C. Reaction was allowed to occur for 1 hour, so that AOI-BM (2-butanone oxime-O-(carbamoylethyl-2-acrylate)) was synthesized as an unsaturated butanone oxime compound 5. AOI-BM is a mixture of 2-butanone oxime-O-(E)-(carbamoylethyl-2-acrylate) and 2-butanone oxime-O-(Z)-(carbamoylethyl-2-acrylate).

<Example 40> (Reaction Product of Oxime Compound and AOI)

An unsaturated butanone oxime compound 6 was synthesized in the same manner as in Example 39, except that the composition of Example 11 (in which the compound (A) was AOI) was used in place of the composition of Example 8.

<Comparative Example 39> (Reaction Product of Oxime Compound and AOI)

An unsaturated butanone oxime compound 7 was synthesized in the same manner as in Example 39, except that the composition of Comparative Example 10 (in which the compound (A) was AOI) was used in place of the composition of Example 8.

<Comparative Example 40> (Reaction Product of Oxime Compound and AOI)

An unsaturated butanone oxime compound 8 was synthesized in the same manner as in Example 39, except that the composition of Comparative Example 16 (in which the compound (A) was AOI) was used in place of the composition of Example 8.

The viscosity of a reaction solution, which includes each of the unsaturated butanone oxime compounds 1 to 8 obtained in Examples 37 to 40 and Comparative Examples 37 to 40, was measured at 25° C. according to JIS-Z 8803:2011 using a tuning-fork vibration viscometer (SV-10 type, manufactured by A & D Company, Limited). The results are shown in Tables 13 and 14.

TABLE 13

| | Unsaturated butanone oxime compound | Composition | Content of compound B in composition ($\times 10^{-4}$ parts by mass) | Viscosity (mPa · sec) |
|---|---|---|---|---|
| Example 37 | 1 | Example 2 | 213 | 0.19 |
| Example 38 | 2 | Example 4 | 489 | 0.24 |
| Comparative Example 37 | 3 | Comparative Example 2 | 2864 | Gelled |
| Comparative Example 38 | 4 | Comparative Example 6 | 11123 | Gelled |

TABLE 14

| | Unsaturated butanone oxime compound | Composition | Content of compound B in composition ($\times 10^{-4}$ parts by mass) | Viscosity (mPa · sec) |
|---|---|---|---|---|
| Example 39 | 5 | Example 8 | 187 | 0.23 |
| Example 40 | 6 | Example 11 | 589 | 0.25 |

TABLE 14-continued

| | Unsaturated butanone oxime compound | Composition | Content of compound B in composition (×10⁻⁴ parts by mass) | Viscosity (mPa · sec) |
|---|---|---|---|---|
| Comparative Example 39 | 7 | Comparative Example 10 | 2654 | Gelled |
| Comparative Example 40 | 8 | Comparative Example 16 | 9065 | Gelled |

As shown in Table 13, in Examples 37 and 38 produced using the composition, in which the compound (B) is contained in an amount of 0.00002 to 0.2 parts by mass with respect to 100 parts by mass of the compound (A), the unsaturated butanone oxime compounds 1 and 2 having appropriate viscosity could be obtained, and the unsaturated butanone oxime compounds could be produced without any problem.

On the other hand, in Comparative Examples 37 and 38 produced by using the composition, in which the content of the compound (B) was higher than 0.2 parts by mass with respect to 100 parts by mass of the compound (A), there was no problem in handling at the raw material stage; however, gelling occurred during the production of the unsaturated butanone oxime compounds 3 and 4.

As shown in Table 14, in Examples 39 and 40 produced using the composition containing 0.00002 to 0.2 parts by mass of the compound (B) with respect to 100 parts by mass of the compound (A), the unsaturated butanone oxime compounds 5 and 6 having appropriate viscosity could be obtained, and the unsaturated butanone oxime compounds could be produced without any problem.

On the other hand, in Comparative Examples 39 and 40 produced by using the composition, in which the content of the compound (B) was higher than 0.2 parts by mass with respect to 100 parts by mass of the compound (A), there was no problem in handling at the raw material stage; however, gelling occurred during the production of the unsaturated butanone oxime compounds 7 and 8.

As shown in the above results, a large difference was observed in terms of behavior of the composition during storage, depending on whether or not the content of the compound (B) is 0.00002 to 0.2 parts by mass with respect to 100 parts by mass of the compound (A). In addition, a large difference was also observed, in terms of viscosity of the unsaturated compound obtained by reacting the composition with any compound of (poly)ol, (poly)amine, (poly)carboxylic acid, (poly)thiol, and oxime compounds, depending on whether or not the content of the compound (B) in the composition is 0.00002 to 0.2 parts by mass with respect to 100 parts by mass of the compound (A).

From these results, it was identified that a concentration of the compound B in the composition was effectively used as an index for determining stability of the composition during storage, and as an index for determining whether or not rapid viscosity increase and/or gelling occurs during the production, in a case where an unsaturated compound is produced using the composition as a raw material.

INDUSTRIAL APPLICABILITY

According to the present invention, there can be provided a composition having excellent stability during storage and use, and a method for producing the same.

The invention claimed is:
1. A composition, comprising:
a compound (A) represented by Formula (1); and
a compound (B) represented by Formula (2),
wherein the compound (B) is contained in an amount of 0.00002 to 0.2 parts by mass with respect to 100 parts by mass of the compound (A), and
a pH of the composition is 1 to 7,

$$(R_1\text{—COO})_n\text{—}R_2\text{—}(NCO)_m \quad (1)$$

(in Formula (1), $R_1$ is an ethylenically unsaturated group having 2 to 7 carbon atoms; $R_2$ is an (m+n)-valent hydrocarbon group having 1 to 7 carbon atoms and optionally contains an ether group; and n and m are each an integer of 1 or 2)

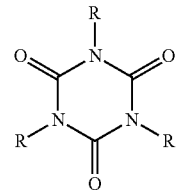

(2)

(in Formula (2), R is (—$R_2$—(OCO—$R_1$), and $R_1$ and $R_2$ are the same as those in Formula (1)).
2. The composition according to claim 1,
wherein the compound (A) is at least one compound selected from the group consisting of 2-methacryloyloxyethyl isocyanate, 2-(isocyanatoethyloxy)ethyl methacrylate, 2-acryloyloxyethyl isocyanate, 2-(isocyanatoethyloxy)ethyl acrylate, and 1,1-bis(acryloyloxymethyl)ethyl isocyanate.
3. The composition according to claim 1, wherein a content of the compound (A) in the composition is 95.0% by mass or higher.
4. The composition according to claim 1, wherein a pH of the composition is 2 to 5.
5. The composition according to claim 1, wherein the content of the compound (A) in the composition is 98.0% to 99.9% by mass.
6. The composition according to claim 1, wherein n and m are each 1.
7. The composition according to claim 1,
wherein $R_1$ is $CH_2$=$C(CH_3)$— or a vinyl group; and $R_2$ is an ethylene group, a methylene group, or —$CH_2CH_2OCH_2CH_2$—.
8. The composition according to claim 1,
wherein $R_1$ is $CH_2$=$C(CH_3)$— or a vinyl group; and $R_2$ is an ethylene group; and n and m are each 1.
9. A method for producing a composition, comprising:
a step of producing a mixture that includes a compound (A) represented by Formula (1) and a compound (B) represented by Formula (2), wherein the compound (B) is contained in an amount of higher than 0.2 parts by mass with respect to 100 parts by mass of the compound (A); and
a purification step, wherein the mixture is subjected to purification by distillation at a reflux ratio of 2.0 to 4.0, a pressure of 1.0 to 10.0 kPa, and a distillation temperature of 90° C. to 140° C., to obtain a purified product, and a pH of the purified product is adjusted to 1 to 7, $$(R_1\text{—COO})_n\text{—}R_2\text{—}(NCO)_m \quad (1)$$

(in Formula (1), $R_1$ is an ethylenically unsaturated group having 2 to 7 carbon atoms; $R_2$ is an (m+n)-valent hydrocarbon group having 1 to 7 carbon atoms and optionally contains an ether group; and n and m are each an integer of 1 or 2)

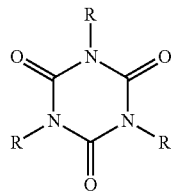

(2)

(in Formula (2), R is (—$R_2$—(OCO—$R_1$), and $R_1$ and $R_2$ are the same as those in Formula (1)).

10. The method according to claim 9, wherein in the composition obtained by the purification step, the compound (B) is contained in an amount of 0.00002 to 0.2 parts by mass with respect to 100 parts by mass of the compound (A).

11. A method for producing an unsaturated compound, comprising:
a step of mixing the composition according to claim 1 with a compound having active hydrogen to react the compound (A) contained in the composition with the compound having active hydrogen, thereby obtaining a reaction product.

12. The method for producing an unsaturated compound according to claim 11, wherein the compound having active hydrogen is an alcohol, a thiol, an amine, or a carboxylic acid.

13. The method for producing an unsaturated compound according to claim 11, wherein the reaction product is an unsaturated urethane compound, an unsaturated thiourethane compound, an unsaturated urea compound, or an unsaturated amide compound.

14. The method for producing an unsaturated compound according to claim 11, wherein the reaction product is any one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

15. A method for producing an unsaturated compound, comprising:
a step of mixing a composition, which comprises
a compound (A) represented by Formula (1) and
a compound (B) represented by Formula (2),
wherein the compound (B) is contained in an amount of 0.00002 to 0.2 parts by mass with respect to 100 parts by mass of the compound (A),
with a compound having active hydrogen to react the compound (A) contained in the composition with the compound having active hydrogen, thereby obtaining a reaction product, $(R_1—COO)_n—R_2—(NCO)_m$      (1)

(in Formula (1), $R_1$ is an ethylenically unsaturated group having 2 to 7 carbon atoms; $R_2$ is an (m+n)-valent hydrocarbon group having 1 to 7 carbon atoms and may contain an ether group; and n and m are each an integer of 1 or 2)

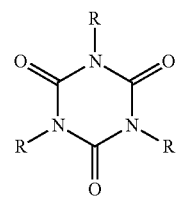

(2)

(in Formula (2), R is (—$R_2$—(OCO—$R_1$), and $R_1$ and $R_2$ are the same as those in Formula (1))
wherein the reaction product is any one selected from the group consisting of 2-butanone oxime-O-(carbamoylethyl-2-methacrylate), 2-[(3,5-dimethylpyrazolyl)carbonylamino]ethyl methacrylate, 2-butanone oxime-O-(carbamoylethyl-2-acrylate), and 2-[(3,5-dimethylpyrazolyl)carbonylamino]ethyl acrylate.

\* \* \* \* \*